United States Patent [19]
Fujita et al.

[11] Patent Number: 5,880,150
[45] Date of Patent: Mar. 9, 1999

[54] ANTIMICROBIAL AGENT CONTAINING ALLYL ISOTHIOCYANATE AND METHOD FOR CONTROLLING RELEASE SPEED OF ALLYL ISOTHIOCYANATE

[75] Inventors: Masao Fujita; Kiyoshi Kamei; Kiyoko Kawazu, all of Sakai-gun; Yuichi Mizukami; Yasushi Sekiyama, both of Osaka, all of Japan

[73] Assignees: The Green Cross Corporation; Rengo Co., Ltd., both of Osaka, Japan

[21] Appl. No.: 481,401

[22] PCT Filed: Nov. 10, 1994

[86] PCT No.: PCT/JP94/01904

§ 371 Date: Jul. 10, 1995

§ 102(e) Date: Jul. 10, 1995

[87] PCT Pub. No.: WO95/12981

PCT Pub. Date: May 8, 1995

[30] Foreign Application Priority Data

Nov. 10, 1993 [JP] Japan ..................... 5-281453

[51] Int. Cl.⁶ .......................... A01N 47/46; A01N 25/00; A01N 25/08; A01N 25/10; A01N 25/18; A01N 25/34; B65D 81/28

[52] U.S. Cl. .......................... 514/514; 514/964; 514/965; 514/781; 424/40; 424/402; 424/404; 424/405; 424/409; 424/411; 424/412; 424/413; 424/443; 424/457; 424/458; 424/461; 424/484; 424/485; 424/486; 424/487; 424/488; 424/494; 428/540; 422/28; 422/40; 71/DIG. 1; 252/8.57; 36/98

[58] Field of Search ............................ 514/514, 964–965; 424/402, 404, 405, 409, 40, 411–413, 443, 457–458, 461, 484–488, 494; 428/305.5, 306.6, 308.4, 320.2, 540; 422/28, 40; 71/DIG. 1, 64.07, 64.11, 64.13; 252/8.57; 36/98

[56] References Cited

U.S. PATENT DOCUMENTS 3,755,064 8/1973 Maierson .................. 428/338

FOREIGN PATENT DOCUMENTS 61-51363 4/1986 Japan .
4-3742 1/1992 Japan .

OTHER PUBLICATIONS

Derwent Abstract of JPA 4–3742 (Jan. 24, 1992).

CABA Abstract Accession No. 81: 27838, abstracting: Carroll et al., "Bioassay of the three isothiocyanates . . . " vol. 73(2), 1980, pp. 321–323.

CABA Abstract Accession No. 81: 24415, abstracting: Bar–Zeev et al., "The response of the adults of the Khapra beetle . . . " Rivista d; Parassitolgia, vol. 40, No. 1/2, 1979, pp. 49–55.

*Primary Examiner*—John Pak
*Attorney, Agent, or Firm*—Sughrue, Mion, Zinn Macpeak & Seas, PLLC

[57] ABSTRACT

An antimicrobial agent comprising allyl isothiocyanate (AIT) packaged in a packaging material having a structure wherein part of the pores of a porous packaging substrate is filled with, or said pores are partially or entirely narrowed by a resin impervious to AIT vapor, and a method for controlling the AIT vapor release speed comprising enclosing AIT in the above-mentioned packaging material. According to the present invention, the AIT vapor release speed can be controlled, whereby enabling sustained release of AIT vapor and persistent effect of antimicrobial action. In addition, the antimicrobial agent of the present invention can be widely applied to food industries and various other fields where breeding and reproduction of deleterious microorganisms pose problems, since it is economical, compact and easy to use. The method of the present invention can control the release of the AIT vapor to the outside of the packaging material, to a desired release speed, whereby the antimicrobial action is effectively exerted while preventing the pollution of the environment and damages to the objects to be treated with the antimicrobial agent, which are caused by AIT vapor. In addition, the antimicrobial action can be sustained for a long time with a small amount of AIT.

20 Claims, 10 Drawing Sheets

ANTIMICROBIAL AGENT CONTAINING ALLYL ISOTHIOCYANATE AND METHOD FOR CONTROLLING RELEASE SPEED OF ALLYL ISOTHIOCYANATE

This application is a 371 of PCT/JP94/01904, filed on Nov. 10, 1994.

TECHNICAL FIELD

The present invention relates to an antimicrobial agent containing allyl isothiocyanate (hereinafter referred to as AIT). More particularly, the present invention relates to a sustained release antimicrobial agent which releases AIT vapor at a certain speed, which is achieved by packaging AIT in a packaging material having a specific structure.

The present invention also relates to a method for controlling the release speed of AIT vapor, comprising enclosing AIT in a packaging material having a specific structure.

BACKGROUND ART

AIT, which is an ingredient of wasasbi, has a superior antimicrobial action such as biocidal, antibacterial and antifungal actions, and shows no harmful effect on human beings. Accordingly, its usefulness as a biocidal agent for foodstuffs and the like has been drawing attention.

AIT itself has a peculiar, strong and sharp smell, and is disadvantageous in that the strong sharp smell adheres to food and the like when used at a high concentration. It is therefore required to effectively exhibit the antimicrobial action in a least possible amount.

Fortunately, AIT vapor from the highly volatile AIT, too, has a strong antimicrobial effect, which allows effective exertion of the antimicrobial action to every corner with only a small amount of the vapor.

Due to the extremely high volatility of AIT, however, the use thereof as it is results in high AIT vapor concentration reached in a short time in the atmospheric gas with which the objects to be treated with the antimicrobial agent are brought into contact, which in turn leads to disadvantageous results that the smell attaches to the objects to be treated, adverse influences are caused by the infiltration of the AIT vapor into the objects to be treated, and the retention of the effects becomes inferior.

For the AIT to be effectively used as an antimicrobial agent, a method is desired which enables free control of the release speed of the AIT vapor and free control of the AIT vapor concentration in the atmospheric gas with which the objects to be treated with the antimicrobial agent are brought into contact, according to the objects to be treated and treatment method. In addition, an antimicrobial agent capable of keeping the effective concentration of AIT in the atmospheric gas for a long time is also desired.

In particular, an antimicrobial agent and a method capable of maintaining a certain release speed for a long time without being influenced by the residual AIT amount are desired. Also, an antimicrobial agent and a method are desired which permit free and easy control of the release speed of the AIT vapor according to the system to be used.

Under the circumstance, agent forms have been proposed, such as an agent form wherein AIT is carried by a carrier such as zeolite, alumina, silica gel, pulp and paper to control the release speed of the AIT vapor, an agent form wherein AIT is packaged in a polyolefin film allowing high permeation of AIT vapor, and an agent form wherein AIT is packaged in a perforated film obtained by perforating a resin film impervious to AIT vapor.

An agent form wherein AIT is carried by a carrier fails to suppress the high volatility of the AIT, resulting in failure to control the release speed. When a film having a high AIT vapor permeability is used, the agent is defective in that a quantitatively constant release speed cannot be realized, since the release speed depends on the remaining amount of AIT, and that it cannot be practically applied to actual products requiring various release speeds, since release speed is controlled by the thickness of the film.

A perforated film is defective in that the release speed is influenced by the residual amount of AIT and constant release speed is difficult to achieve when AIT vapor is to be released by small portions, and that an agent showing little dispersion in release speed is difficult to manufacture.

As described above, a method permitting free control of the AIT vapor release speed without dispersion and a method permitting portionwise release of an effective amount of AIT vapor at a constant speed have not existed.

DISCLOSURE OF THE INVENTION

Accordingly, it is an object of the present invention to provide an antimicrobial agent capable of controlling the permeability of AIT vapor, in particular, an agent permitting release of an effective amount of AIT vapor for a long time, i.e., a so-called sustained release antimicrobial agent.

Another object of the present invention is to provide a method for controlling the release speed of AIT vapor.

In view of the above-mentioned problems, the present inventors have conducted intensive studies for the development of a useful and practical AIT-containing antimicrobial agent, and found that the permeability of AIT vapor can be controlled by packaging AIT in a packaging material having the specific structure mentioned below, that an antimicrobial agent having such construction and stable quality can be produced easily and economically, and that sustained release of the effective amount of AIT can be achieved in general, practical use by packaging AIT in said packaging material, which resulted in the completion of the invention.

The present invention provides an antimicrobial agent comprising allyl isothiocyanate packaged in a packaging material having a structure wherein part of the pores of a porous packaging substrate is filled with, or said pores are partially or entirely narrowed by a resin impervious to allyl isothiocyanate vapor.

The present invention also provides a method for controlling the AIT vapor release speed by enclosing AIT in a packaging material having the above-mentioned specific structure.

BRIEF DESCRIPTION OF THE DRAWINGS

1. An AIT vapor release curve of an antimicrobial agent comprising a packaging substrate 1 as a packaging material.
2. An AIT vapor release curve of an antimicrobial agent comprising a polyethylene laminated cellophane as a packaging material.
3. An AIT vapor release curve of an antimicrobial agent comprising a cellulose-modified paper ① as a packaging material.
4. An AIT vapor release curve of an antimicrobial agent comprising a cellulose-modified paper ② as a packaging material.

5. An AIT vapor release curve of an antimicrobial agent comprising a cellulose-modified paper ③ as a packaging material.

6. An AIT vapor release curve of an antimicrobial agent comprising a packaging substrate 2 as a packaging material.
7. An AIT vapor release curve of an antimicrobial agent comprising a polyethylene laminated cellophane as a packaging material.
8. An AIT vapor release curve of an antimicrobial agent comprising a cellulose-modified nonwoven fabric ① as a packaging material.
9. An AIT vapor release curve of an antimicrobial agent comprising a cellulose-modified nonwoven fabric ② as a packaging material.
10. An AIT vapor release curve of an antimicrobial agent comprising a cellulose-modified nonwoven fabric ③ as a packaging material.

11. An AIT vapor release curve of an antimicrobial agent comprising a PVA-modified nonwoven fabric ③ as a packaging material.
12. An AIT vapor release curve of an antimicrobial agent comprising a PVA-modified nonwoven fabric ② as a packaging material.
13. An AIT vapor release curve of an antimicrobial agent comprising a PVA-modified nonwoven fabric ① as a packaging material.

14. An AIT vapor release curve of an AIT-impregnated support (calcium silicate particles).
15. An AIT vapor release curve of an AIT-impregnated support (radiolite powder).
16. An AIT vapor release curve of an AIT-impregnated support (foamed cellulose particles).

DETAILED DESCRIPTION OF THE INVENTION

The antimicrobial agent of the present invention is explained in the following.

(1) Packaging material

The packaging substrate to be used in the present invention is porous. The number, size and structure of the pores are not particularly limited as long as the packaging substrate can carry a resin and can sufficiently permeate the AIT vapor.

The pores consist of pores based on the structure of the material itself of the packaging substrate and those formed according to the production method of the packaging substrate.

Examples of the packaging substrate generally include thin substrates formed from fiber materials, such as paper and nonwoven fabric. The material therefor can be a hydrophilic material, a hydrophobic material, or a mixture thereof, with preference given to a hydrophilic material.

The hydrophilic material is not particularly limited and is exemplified by natural pulp such as broadleaf pulp and conifer pulp, bast fibers such as Manila hemp, paper mulberry and paper bush, and natural, semisynthetic and synthetic fibers such as cotton linter, rayon, Cupra, polyvinyl alcohol and Vinylon, which may be used alone or in combination.

Examples of the hydrophobic material include polyethylene, polyester and polypropylene.

The shape, size, thickness, weight and production method of the packaging substrate to be used are not particularly limited. In view of easy handling, the substrate generally weighs 10–100 g/m², preferably 10–50 g/m² and generally has a thickness of 10–100 μm, preferably 20–70 μm.

The packaging material to be used in the present invention has a specific structure characterized in that part of the numerous pores in the packaging substrate are filled with, or said pores are partially or entirely narrowed by a resin impervious to AIT vapor.

Namely, the packaging material to be used in the present invention has a structure wherein pores are filled with, or narrowed by a resin impervious to AIT vapor, which has entered the numerous pores in the above-mentioned packaging substrate, and shows small air permeability.

With regard to the present invention, the resin impervious to AIT vapor preferably achieves, when formed into a 10–30 μm thick film, an AIT vapor permeation rate of not more than 50 mg/day·cm² at 20° C. under 65% RH. Examples of such resin include cellulose regenerated from viscose, cellulose regenerated from a cellulose cuprammonium solution, cellulose acetate, carboxymethyl cellulose, starch, polyvinyl alcohol, vinylidene chloride and acrylic resin.

The resin is selected in consideration of the affinity for the packaging substrate to be used, applicability, AIT vapor permeability of the coated substrate, and slip property and heat sealing property required during packaging and when in use. Preferred is cellulose regenerated from viscose.

The method for filling the pores in the packaging substrate and the method for narrowing the pores with the aforementioned resin are not particularly limited. It is generally a method comprising coating a solution of the aforementioned resin on a packaging substrate.

The coating method is not subject to particular limitation and is appropriately selected according to the viscosity of the resin solution to be used and the desired amount of the adhered resin. Examples thereof include roll coating using reverse rolls or gravure rolls, bar coating, rod coating and dip coating.

A packaging substrate applied with the resin is dried and prepared into the packaging material of the present invention.

When cellulose regenerated from viscose or cellulose regenerated from a cellulose cuprammonium solution is used as the resin, the viscose or the copper oxide ammonium solution is coated on a packaging substrate and subjected to a regeneration treatment using an acid to give regenerated cellulose. The cellulose is subjected to desulfuration and bleaching where necessary, washed with water, subjected to softening treatment with a softener such as triethylene glycol and dried. For regeneration using an acid, a conventional method such as "regeneration cellulose preparation" can be used.

The packaging material thus prepared has a structure wherein part of the numerous pores in the starting material packaging substrate are filled with said resin, or said pores are partially or entirely narrowed by the resin to form fine pores, whereby air permeation is suppressed in comparison with that with the original packaging substrate. Using such packaging material, the permeation of AIT vapor can be suppressed in comparison with that with the original packaging substrate.

The air permeation of the packaging material varies depending on the size, density and total area of the fine pores formed in the packaging material. Accordingly, the air permeation can be adequately adjusted by controlling such conditions.

The permeability of AIT vapor, too, can be adjusted to the desired level by controlling the size and total area etc. of the fine pores formed in the packaging material.

With respect to the packaging material treated with said resin and its porosity, the number, size, density and total area of the pores can be freely controlled by appropriately selecting and combining the kind of packaging substrate, the kind of resin, and the concentration, viscosity, the impregnated amount and the method of application of the resin solution to be coated. For example, when permeability of AIT vapor is to be made smaller, a packaging substrate having smaller voids between fibers is selected, or the amount of the resin to be impregnated is increased, or other method is employed.

The AIT vapor permeation from the packaging material of the present invention which has been treated as described above is evaluated by determining the air permeation from the packaging material according to the method as defined in JIS P 8117.

While part of the pores are filled with a resin impervious to allyl isothiocyanate vapor, or said pores are partially or entirely narrowed thereby, the degree of filling and narrowing is appropriately determined according to the desired air permeability.

In the present invention, the air permeation of the packaging material is generally 1,000–500,000 seconds, preferably 3,000–200,000 seconds, and more preferably 10,000–100,000 seconds. It is preferable that the filling or narrowing using the resin be performed to achieve such air permeation.

The packaging material to be used in the present invention may be laminated with a perforated film or a polyolefin heat sealing film as necessary.

Laminating with a perforated film is advantageous when a desired AIT vapor permeation cannot be achieved by resin coating alone, in the event the packaging substrate is thick and allows a greater AIT vapor permeation. In addition, laminating enables easier and delicate adjustment of the AIT vapor permeability. By a perforated film is meant a film having regular pores formed by mechanical or thermal treatment, and is exemplified by perforated polyethylene films manufactured by Shin Nippon Aruku Corp.

In addition, laminating with a heat sealing film can achieve heat sealing strength. The laminating can be done by a conventional method, and may be done before or after the treatment of the packaging substrate with the resin.

The packaging material to be used in the present invention may be subjected to water repellent treatment or water resistant treatment.

Such treatment can be performed by a conventional method before or after the resin treatment of the packaging substrate. Specifically, a packaging material is soaked in a solution containing a water repellent agent or waterproof agent at a predetermined concentration, squeezed to remove excess solution and dried.

The packaging material of the present invention can control the AIT vapor permeability by adjusting the size, density and total area of the fine pores formed by treating the packaging substrate with the resin, as described above, and has an extremely simple structure as compared with the conventional packaging materials of this kind. The method for coating the resin on the packaging substrate is a conventional method widely used, thus enabling easy production of the material having stable properties at lower costs.

By packaging AIT in the packaging material thus produced, the amount and speed of the AIT vapor to be released to the outside of the packaging material can be adjusted to a certain level.

(2) AIT to be packaged in the above-mentioned packaging material

The AIT to be packaged in the above-mentioned packaging material is described in the following.

The AIT to be used in the present invention may be natural or synthetic. It is not limited to an agent consisting of 100% AIT, but may be a composition containing AIT. When the antimicrobial agent of the present invention is used for foodstuffs, however, a naturally occurring AIT is preferable. There is no limitation imposed on the synthesis method of AIT. A general method comprises heat-reacting allyl iodide or allyl bromide with sodium thiocyanate in ethanol.

The form of the AIT to be packaged in the above-mentioned packaging material is exemplified by liquid (oil, aqueous solution), or powder, granules or solid, which are prepared by having the liquid carried by a solid.

The carrier for carrying AIT is exemplified by pulp, paper, cellulose particles (in particular, foamed cellulose beads), zeolite, alumina, silica gel and calcium silicate, with preference given to foamed cellulose beads. Preferable foamed cellulose beads include porous cellulose particles composed of cellulose and having a spherical shape of the size of not less than 0.05 m/m, preferably not less than 0.5 m/m, whose surface has numerous cracks and small holes. The particles also comprise numerous void pores in the inside and are porous as a whole, and 90% or above of the entire pore volume is fine pores having a radius of not less than 2.5 $\mu$m, as identified from a fine pore radius distribution and pore volume, determined by mercury porosimeter method. More preferably the particles have a bulk density of 0.05–0.5 g/cc, a specific surface area of 1–30 cm$^2$/g, a water holding capacity of 4–15 g/g and an oil holding capacity of 4–10 g/g, such as Viscopearl (manufactured by RENGO CO., LTD.).

The amount of the AIT to be packaged in the above-mentioned packaging material is appropriately selected and adjusted according to the balance of the desired duration of the antimicrobial action, and AIT vapor concentration in the desired system (region wherein antimicrobial action is needed). When the surface area (effective surface area) of the AIT vapor release region is 1–300 m$^2$, AIT volume is desirably 0.1–50 g, in which range an effective amount of AIT vapor is persistently released.

(3) Packaging form

The packaging form for packaging the AIT in the above-mentioned packaging material is not particularly limited as long as AIT is enclosed in a bag manufactured therefrom. The form of the bag includes three sided seal type, four sided seal type and pillow type.

The method for bag making is not particularly limited and may include a method wherein an adhesive is used, and a heat sealing method, with preference given to heat sealing method from the aspects of productivity and stability.

The surface area (effective area) of the AIT vapor release region in the packaging material is 1–300 cm$^2$, preferably 5–200 cm$^2$, and more preferably 10–100 cm$^2$.

The antimicrobial action in the present invention includes biocidal, bacteriostatic and bacteria-preventing action on aerobic bacteria and anaerobic bacteria; antimicrobial action against mold, such as moldeidal, moldstatic and mold-preventing action; freshness degradation-preventing action on foodstuffs; and an action of a preservative which aims at retention of freshness.

The microorganisms to be treated with the antimicrobial agent of the present invention include, for example, fungi such as mold and yeast, bacteria such as Staphylococcus, *Escherichia coli, Salmonella typhi*, Vibrio, spore, algae and other deleterious microorganisms.

The objects to be treated with the antimicrobial agent of the present invention include, for example, foodstuffs and various other articles facing problems caused by growth and reproduction of deleterious microorganisms. Specific examples thereof include livestock products, marine products, agricultural products, cooked foods, processed foods, diet, leather articles (e.g. shoes), books, art objects (especially antique) and the like.

The method of the present invention comprises placing AIT in the form and amount appropriately determined, in a packaging material prepared to exhibit a desired AIT vapor permeability.

For example, the antimicrobial agent of the present invention is concurrently placed in a thermostatic chamber (e.g. refrigerator), food transport containers, food storage containers, leather article storage containers, leather article transport containers, book storage containers or rooms, and art object storage containers or rooms.

When the antimicrobial agent of the present invention is used for shoes, for example, it is preferable that said antimicrobial agent be placed in an individual shoe during transport and storage. In this way, development of mold and bacteria during transport and storage of shoes can be significantly suppressed.

When the antimicrobial agent of the present invention is used in a refrigerator, one or more dispensed packages of the antimicrobial agent in an appropriate amount according to the volume of the refrigerator are placed therein, thereby to suppress the development of bacteria and bad odor in the refrigerator.

When used for leather articles, particularly during storage of shoes, the air permeation is generally 5,000–100,000 seconds, preferably 10,000–70,000 seconds and more preferably 20,000–50,000 seconds. The surface area of the AIT vapor release region is generally 1–15 cm$^2$, preferably 2–10 cm$^2$, and more preferably 4–8 cm$^2$. The amount of the AIT is generally 0.1–2 g, preferably 0.2–1 g, and more preferably 0.3–0.8 g.

The air permeation for use in a thermostatic chamber is generally 5,000–100,000 seconds, preferably 10,000–70,000 seconds, and more preferably 20,000–50,000 seconds. The surface area of the AIT vapor release region is generally 3–45 cm$^2$, preferably 6–30 cm$^2$, and more preferably 10–25 cm$^2$. The volume of the AIT is generally 0.3–6 g, preferably 0.5–3 g, and more preferably 0.9–2 g.

By appropriately selecting and combining the kind of the packaging substrate to be used, the kind of resin, the amount of the resin to be applied and the method of coating the resin solution, the size, density and total area of the pores in the packaging material can be appropriately controlled, whereby packaging materials having a desired AIT vapor permeability can be prepared. Specific preparation methods include the aforementioned methods.

The form and amount of the AIT to be enclosed inside thereof are appropriately determined according to the object of use and the permeability of AIT vapor through the packaging material to be used. The form of AIT is liquid (e.g. oil, aqueous solution), powder, granules or solid, as mentioned above.

Enclosing AIT in a packaging material means almost the same as the aforementioned packaging, and the enclosing is performed by a method similar to that of the aforesaid packaging method.

The antimicrobial agent of the present invention exhibits various AIT vapor release speeds according to the combinations of various preparation conditions such as the size, density and total area of the pores in the packaging material, and the amount and form of AIT to be enclosed therein. The release speed is about quantitatively constant, without being influenced by the amount of AIT therein. Consequently, it is possible to release the AIT vapor in a sustained manner for a long time at a certain, suppressed release speed depending on the selected conditions. Accordingly, the antimicrobial agent of the present invention enables a long-term sustained release of the antimicrobial action with a small amount of AIT.

The structure of the pores such as the pore size in the packaging material, which is one of the factors for controlling the AIT vapor release speed, is easily adjusted by the kind of the packaging substrate to be used, the kind of resin, the amount of the impregnated resin, a method of coating the resin solution and a dipping method. Accordingly, by appropriately modifying the preparation conditions, and further by appropriately determining the form and amount of AIT to be enclosed therein, antimicrobial agents having various AIT vapor release speeds can be prepared.

Said antimicrobial agent can be prepared with ease by a conventional production method, thereby enabling production of the agents having a certain quality with good reproducibility.

The packaging material can be prepared with ease at extremely low costs. Accordingly, the antimicrobial agent of the present invention is economically superior.

In addition, the antimicrobial agent of the present invention can be widely applied to various fields inclusive of food industries, where breeding and reproduction of deleterious microorganisms pose problems, since it is compact, does not occupy much room and is easy to carry. For example, the antimicrobial agent of the present invention can be advantageously used for the prevention of molds from developing on foodstuffs, prevention of putrefaction and fermentation of foodstuffs, prevention of degradation of freshness, suppression of food poisoning bacteria, protection against insects, storage of leather articles, and books and art objects (especially antique).

According to the method for controlling the release speed of the AIT vapor of the present invention, AIT vapor can be released to the outside of the packaging material at a certain desired speed. The release speed can be adjusted to a desired level by an easy method including appropriately selecting and combining the preparation conditions of packaging materials (e.g. the kind of packaging substrate and resin, the amount of resin to be coated and method for coating the resin), and the amount and the form of AIT.

According to the method of the present invention, it is possible to release AIT vapor at a controlled certain speed, whereby the pollution of the environment and damages to the objects to be treated with the antimicrobial agent, which are caused by AIT vapor, are suppressed, while effectively exerting the antimicrobial action for a long time with a small amount of AIT.

The present invention is described in the following by referring to Examples and Experimental Examples.

EXAMPLE (1) Preparation of packaging substrate

The following packaging substrates were prepared.

Packaging substrate 1: Polyethylene was laminated (thickness 20 μm) on a paper composed of wood pulp (50%) and Manila hemp (50%) and weighing 20 g/m² by an extrusion laminater.

Packaging substrate 2: A sheet composed of rayon (20%) and a synthetic pulp (SWP, 80%) made from polyethylene (PE), and weighing 40 g/m² was prepared and subjected to heat treatment (150° C.×1 min) in a hot air drier to give a packaging substrate of a nonwoven fabric.

(2) Preparation of packaging material—1

A viscose solution having a different cellulose concentration was roll-coated on the surface of these packaging substrates 1 and 2 to give three kinds of packaging materials having a different AIT vapor permeability (or permeation).

Specifically, a viscose solution for cellophane production (9.5% cellulose concentration, 6.5% alkali concentration, viscosity 5,000 cp at 20° C.) was diluted with water to give a coating solution having a cellulose concentration of 6%, 4.5% or 3%. The solution was coated on a packaging substrate using a roll coater under the same mechanical conditions. Then, the substrates were subjected to a solidification treatment in a coagulation bath mainly composed of sulfuric acid, subjected to regeneration of cellulose in a regeneration bath mainly composed of sulfuric acid, subjected to desulfuration, washed with water and dried with a cylinder drier to give the packaging materials of the present invention.

The amount (g/m²) of the regenerated cellulose which adhered to the respective packaging materials thus obtained and air permeation (sec) determined by Gurley densometer according to the method defined in JIS P 8117 are shown in the following Table. The values in the Table are the average values at 10 sites (n=10) in the packaging materials.

| packaging material | | viscose concentration (%) | amount of adhered regenerated cellulose (g/m²) | permeation (second) |
|---|---|---|---|---|
| packaging substrate 1 (paper) | | 0 | 0 | |
| cellulose-modified paper | ① | 3 | 0.5 | ∞ |
| cellulose-modified paper | ② | 4.5 | 0.8 | ∞ |
| cellulose-modified paper | ③ | 6 | 1.4 | ∞ |
| packaging substrate 2 (nonwoven fabric) | | 0 | 0 | about 0.1 |
| cellulose-modified nonwoven fabric | ① | 3 | 0.8 | 3000 |
| cellulose-modified nonwoven fabric | ② | 4.5 | 1.2 | 7500 |
| cellulose-modified nonwoven fabric | ③ | 6 | 1.8 | 12000 |

(3) Preparation of packaging material—2

A polyvinyl alcohol (PVA) aqueous solution having a different PVA concentration was roll-coated on the surface of the packaging substrates 2 to give three kinds of packaging materials having a different air permeability.

Specifically, a PVA (Kuraray POVAL 117) aqueous solution having a PVA concentration of 1.5%, 3% or 5% was prepared, coated on the surface of the packaging substrate 2 under the same mechanical conditions of a roll coater. Then, the substrates were dried using a hot air drier at 100° C. to give the packaging materials of the present invention.

The amount (g/m²) of the PVA which adhered to the packaging materials thus obtained and air permeation (sec) determined by Gurley densometer according to the method defined in JIS P 8117 are shown in the following Table.

| packaging material | | PVA concentration (%) | amount of PVA adhered (g/m²) | permeation (second) |
|---|---|---|---|---|
| packaging substrate 1 (nonwoven fabric) | | 0 | 0 | about 0.1 |
| PVA-modified nonwoven fabric | ① | 1.5 | 0.7 | 1000 |
| PVA-modified nonwoven fabric | ② | 3 | 1.0 | 4000 |
| PVA-modified nonwoven fabric | ③ | 5 | 1.6 | 7000 |

(4) Preparation of support impregnated with AIT

The respective carriers (a)–(c) (1 g) mentioned below were impregnated with 10 ml of an AIT reagent (reagent corresponding to a best grade product, manufactured by Kanto Kagaku Corp.) under reduced pressure for 5 minutes. The excess AIT was removed by centrifugation to give various supports (a, b, c) impregnated with AIT.

Carrier: a. calcium silicate particles (5–6 m/m diameter, manufactured by Takasago Koryo Corp.)

b. radiolite powder (10–50 μm diameter, manufactured by Showa Kagaku Kogyo Corp.)

c. foamed cellulose beads (3–4 m/m diameter, manufactured by RENGO CO., LTD.)

(5) Antimicrobial agent

The respective 9 kinds of packaging materials prepared in the above-mentioned Example (2) and (3) were cut to have a surface area (effective area) of the AIT vapor release region of 2 cm², 32 cm², 200 cm² or 300 cm². The materials were folded at the center of the longer side, and sealed at two sides by a heat-sealer to give one-mouthed bags.

An AIT reagent (3 g, reagent corresponding to a best grade product, manufactured by Kanto Kagaku Corp.) or a support (a, b or c) impregnated with AIT which was produced in Preparation Examples was placed in the aforementioned 36 kinds of packaging materials and the opening was heat-sealed to give the total of 144 kinds of antimicrobial agents.

REFERENCE EXAMPLE

For comparison with the antimicrobial agent of the present invention in the following Experimental Examples, an AIT reagent or a support impregnated with AIT was enclosed in a packaging substrate 1, packaging substrate 2 or polyethylene laminated cellophane [an extrusion laminate of cellophane (20 μm thick, manufactured by RENGO CO., LTD.)with a 20 μm thick PE], instead of the packaging material of the present invention.

The following Experiments were performed to measure the amount of the AIT vapor release from the antimicrobial agent of the present invention and the agents prepared in Reference Example.

The antimicrobial agents subjected to the experiments in the following Experimental Examples 1–3 are shown in the following Table.

| packaging material | | AIT to be enclosed |
|---|---|---|
| [Experimental Example 1] | | |
| packaging substrate 1 | | AIT reagent (liquid) |
| cellulose-modified paper | ① | " |
| cellulose-modified paper | ② | " |
| cellulose-modified paper | ③ | " |
| polyethylene laminated cellophane | | " |
| [Experimental Example 2] | | |
| packaging substrate 2 | | foamed cellulose beads impregnated with AIT |
| cellulose-modified nonwoven fabric | ① | foamed cellulose beads impregnated with AIT |
| cellulose-modified nonwoven fabric | ② | foamed cellulose beads impregnated with AIT |
| cellulose-modified nonwoven fabric | ③ | foamed cellulose beads impregnated with AIT |
| polyethylene laminated cellophane | | foamed cellulose beads impregnated with AIT |
| [Experimental Example 3] | | |
| PVA-modified nonwoven fabric | ① | foamed cellulose beads impregnated with AIT |
| PVA-modified nonwoven fabric | ② | foamed cellulose beads impregnated with AIT |
| PVA-modified nonwoven fabric | ③ | foamed cellulose beads impregnated with AIT |

Figure 1:
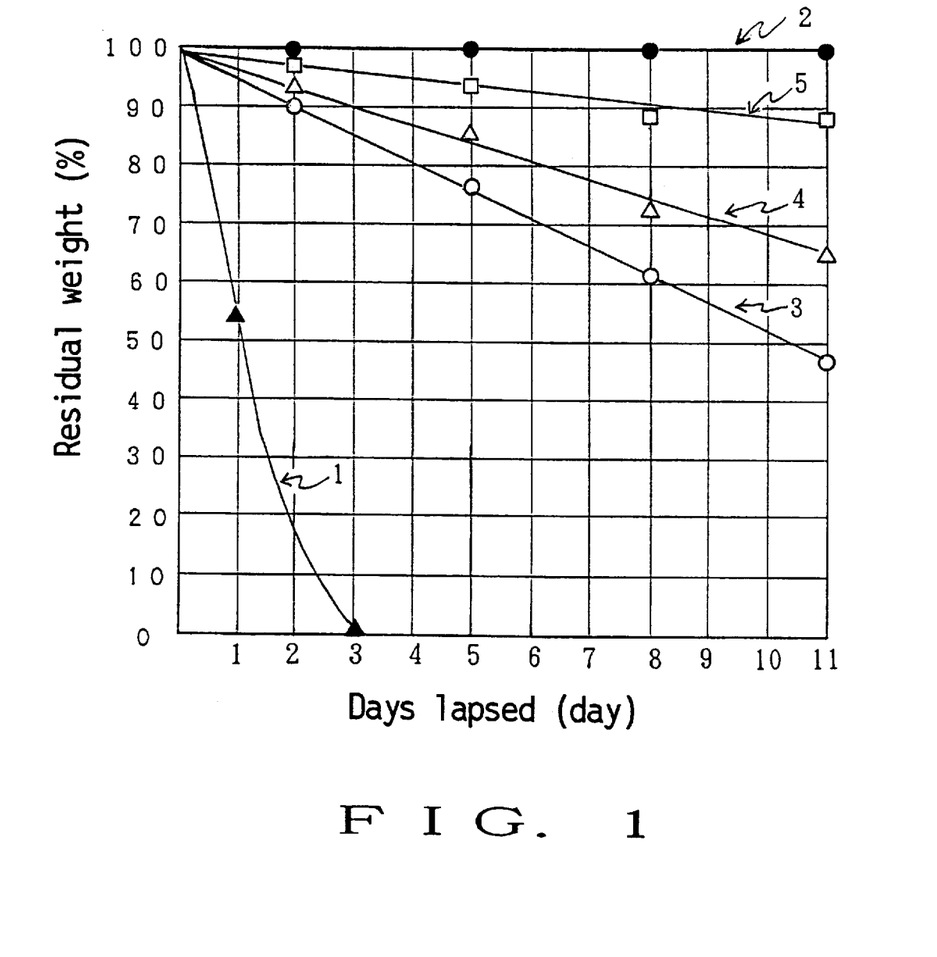
FIG. 1 is a graph showing the release speed of AIT vapor from the antimicrobial agents (cellulose-modified paper) of the present invention as used in Experimental Example 1, wherein the symbols 1 to 5 mean the following.

Experimental Example 1
Control of sustained release and release speed of AIT vapor by cellulose-modified paper The antimicrobial agents comprising the cellulose-modified paper ①, ② or ③, packaging substrate 1 or polyethylene laminated cellophane as obtained in Example and Reference Example as a packaging material, and a liquid AIT reagent (3 g) therein were placed in a thermostatic chamber at 30° C., and changes in weight were measured with the lapse of time, based on which the amount of the AIT vapor release was calculated. The results are shown in FIG. 1.

When the packaging substrate 1 was used, AIT vapor mostly just passed through, whereas the cellulose-modified paper ①, ② or ③ released the AIT vapor at a certain speed for a long time. From these results, it was found that the release speed can be freely controlled by the amount of the cellulose adhered.

Figure 2:
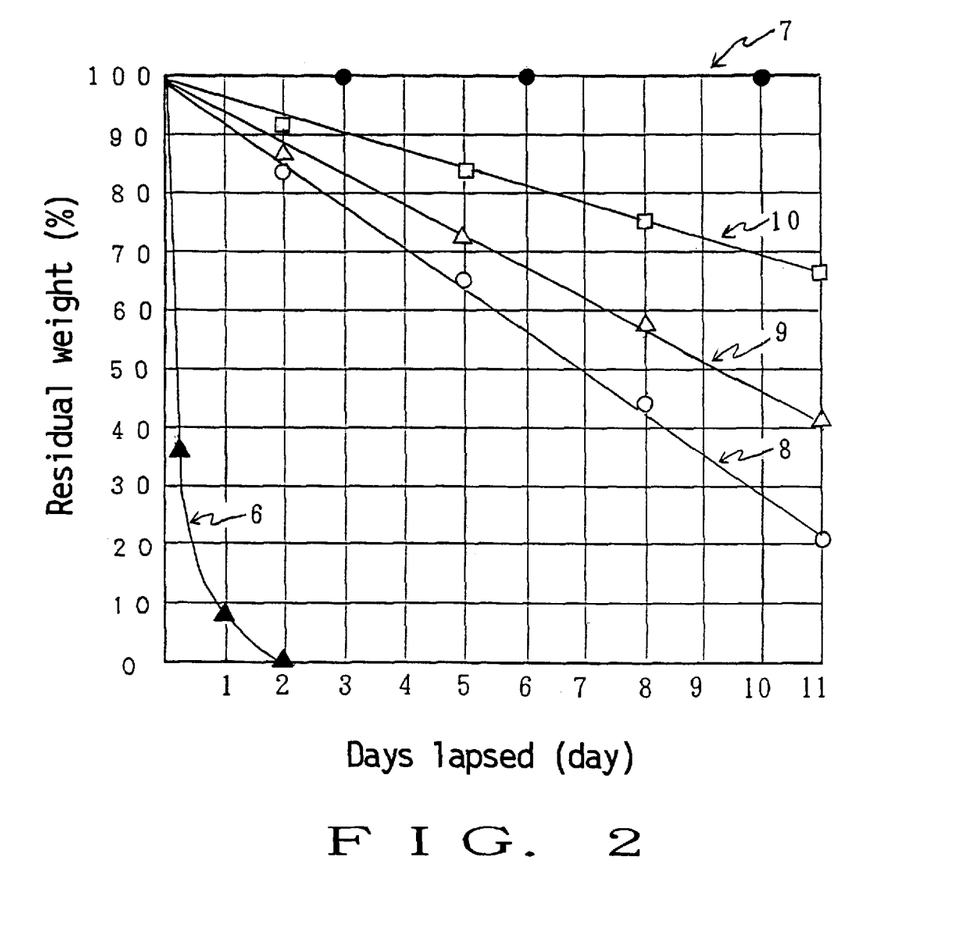
FIG. 2 is a graph showing the release speed of AIT vapor from the antimicrobial agents (cellulose-modified nonwoven fabric) of the present invention as used in Experimental Example 2, wherein the symbols 6 to 10 mean the following.

Experimental Example 2
Control of sustained release and release speed of AIT vapor by cellulose-modified nonwoven fabric Using the respective antimicrobial agents comprising, as a packaging material, the cellulose-modified nonwoven fabric ①, ② or ③, packaging substrate 2 or polyethylene laminated cellophane as obtained in Example and Reference Example, and AIT-impregnated foamed cellulose particles (ca. 5 cc consisting of about 1 g of carrier and 1.5 g of AIT) therein, the same experiment as in Experimental Example 1 was performed. The results are shown in FIG. 2.

When the packaging substrate 2 was used, AIT vapor was rapidly released, whereas the cellulose-modified nonwoven fabrics ①, ② and ③ released the AIT vapor at a certain speed for a long time. From these results, it was found that the release speed can be freely controlled by the amount of the cellulose adhered.

Figure 3:
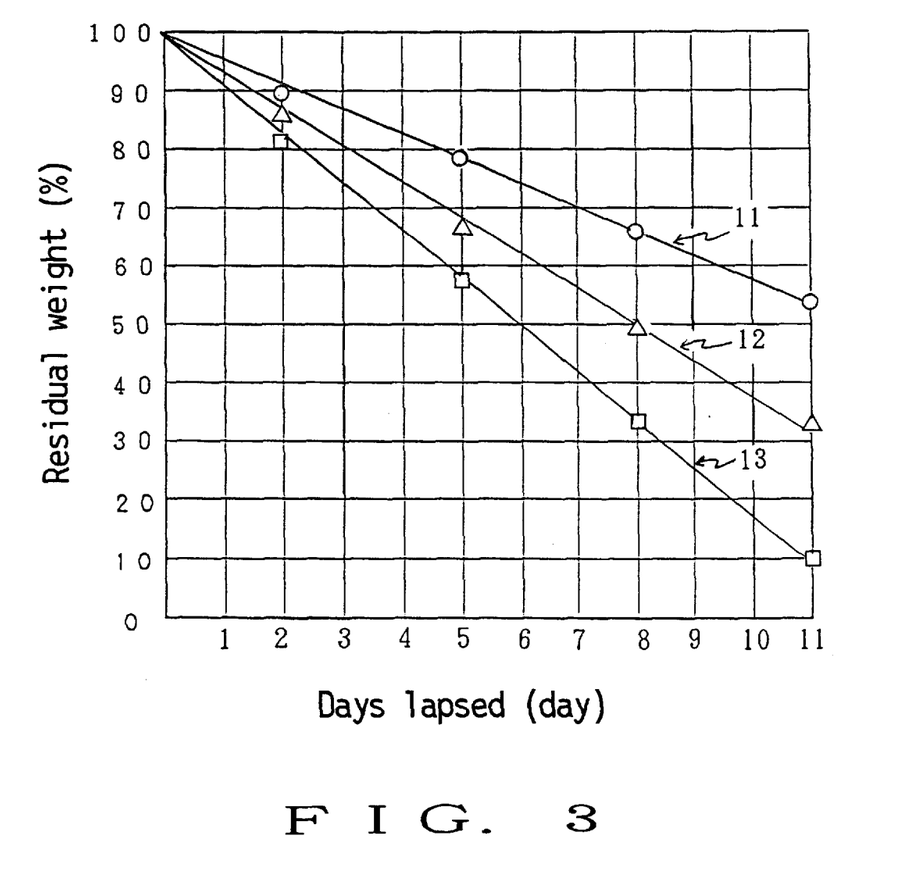
FIG. 3 is a graph showing the release speed of AIT vapor from the antimicrobial agents (PVA-modified nonwoven fabric) of the present invention as used in Experimental Example 3, wherein the symbols 11 to 13 mean the following.

Experimental Example 3
Control of sustained release and release speed of AIT vapor by PVA-modified nonwoven fabric Using the antimicrobial agents comprising, as a packaging material, the PVA-modified nonwoven fabric ①, ② or ③ as obtained in Example, and AIT-impregnated foamed cellulose particles (ca. 5 cc consisting of about 1 g of carrier and 1.5 g of AIT) therein, the same experiment as in Experimental Example 2 was performed. The results are shown in FIG. 3.

The PVA-modified nonwoven fabrics ①, ② and ③ released the AIT vapor at a certain speed for a long time. From these results, it was found that the release speed can be freely controlled by the amount of the PVA adhered.

Comparative Example
Release of AIT vapor from each support

Figure 4:
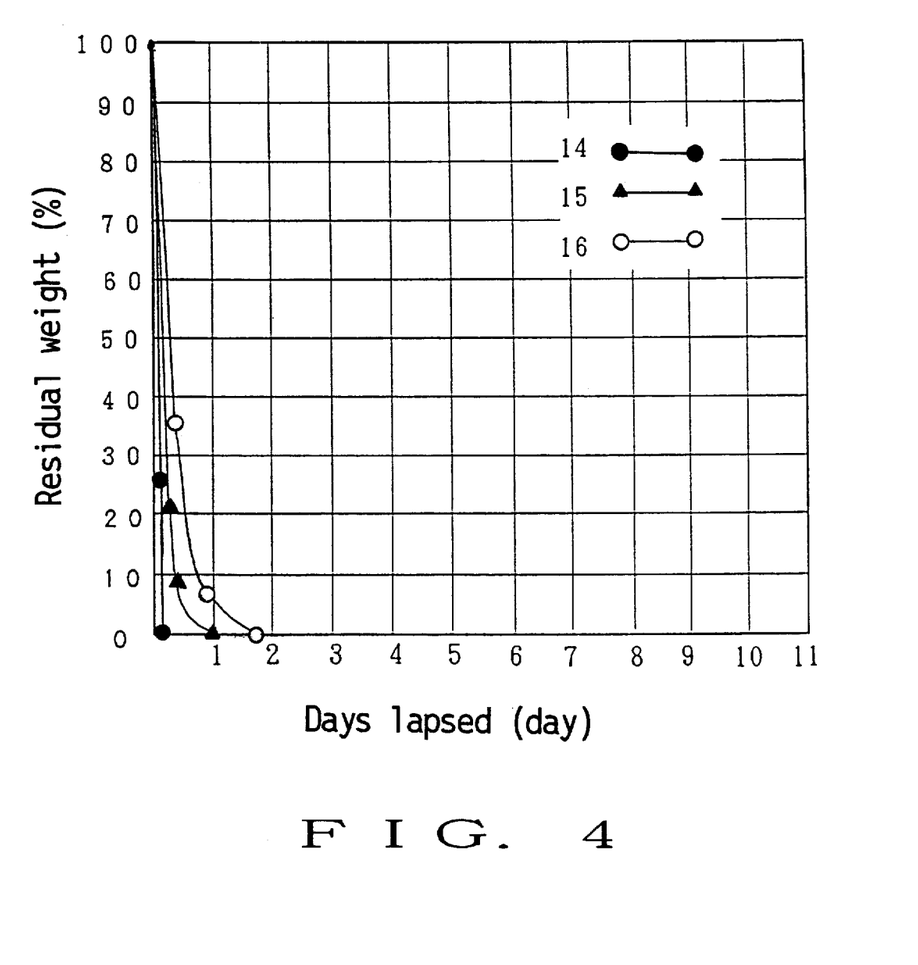
FIG. 4 is a graph showing the release speed of AIT vapor from the AIT-impregnated supports as used in Comparative Experiment, wherein the symbols 14 to 16 mean the following.
Figure 5:
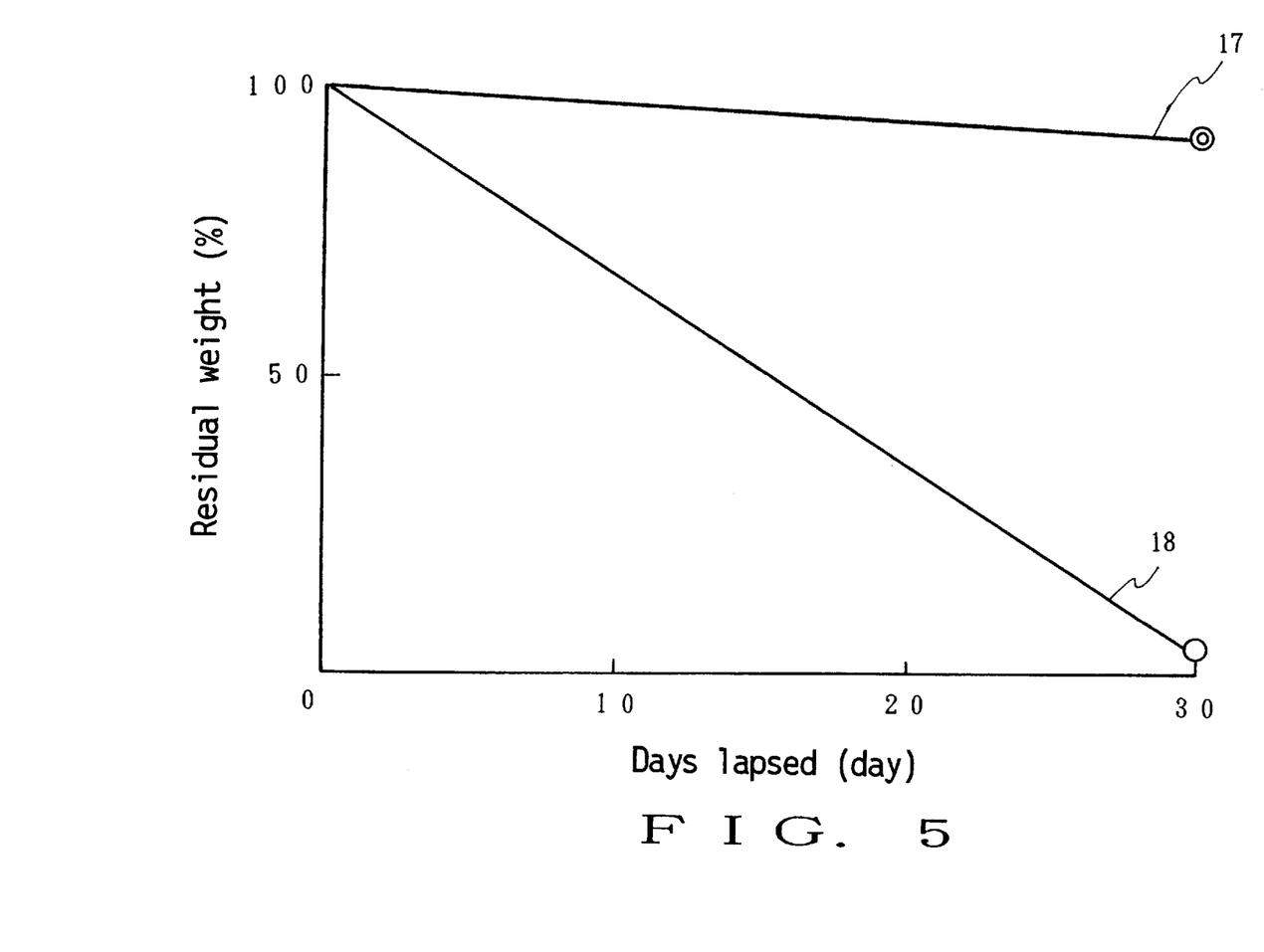
FIG. 5 is a graph showing the release speed of AIT vapor from antimicrobial agents comprising cellulose beads impregnated with AIT (0.2 g), enclosed in packaging materials having various air permeabilities [21,000 seconds (18 in the Figure) and 400,000 seconds (17 in the Figure)] and an effective surface area of 32 cm².
Figure 6:
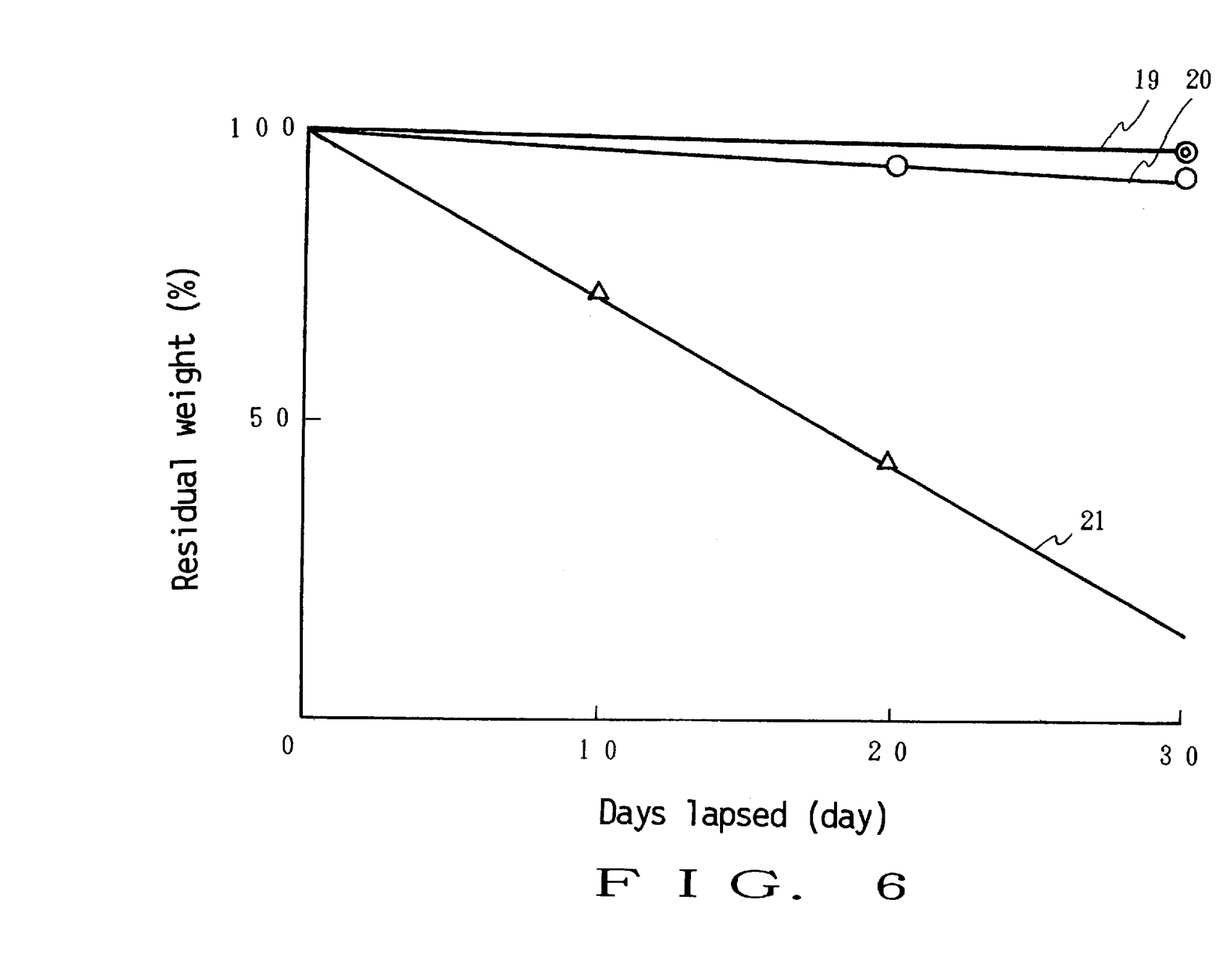
FIG. 6 is a graph showing the release speed of AIT vapor from antimicrobial agents comprising cellulose beads impregnated with AIT (2 g), enclosed in packaging materials having various air permeabilities [1,500 seconds (21 in the Figure), 21,000 seconds (20 in the Figure) and 400,000 seconds (19 in the Figure)] and an effective surface area of 32 cm².
Figure 7:
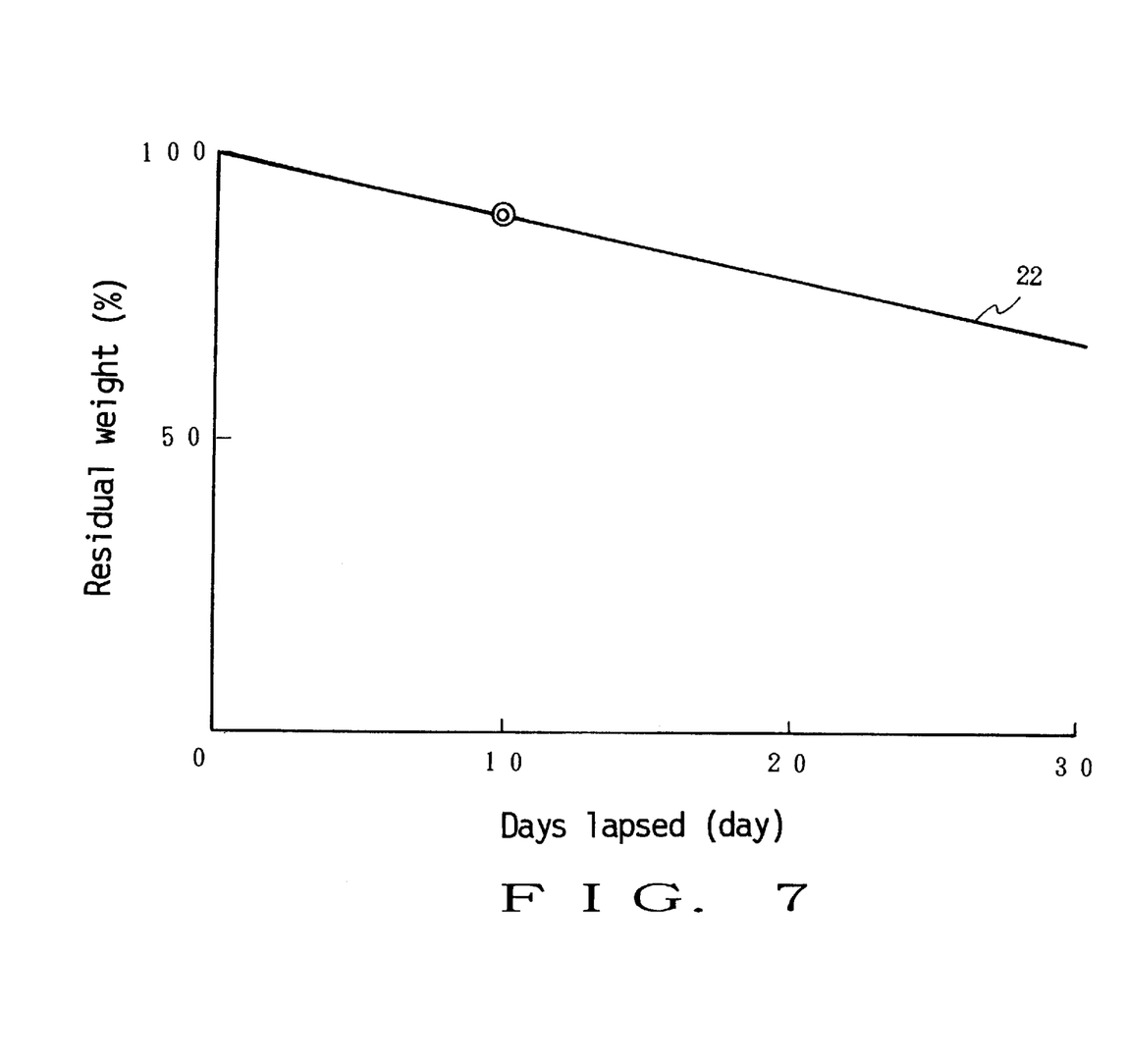
FIG. 7 is a graph showing the release speed of AIT vapor from an antimicrobial agent comprising cellulose beads impregnated with AIT (0.2 g), enclosed in a packaging material having an air permeability of 400,000 seconds (22 in the Figure) and an effective surface area of 200 cm².
Figure 8:
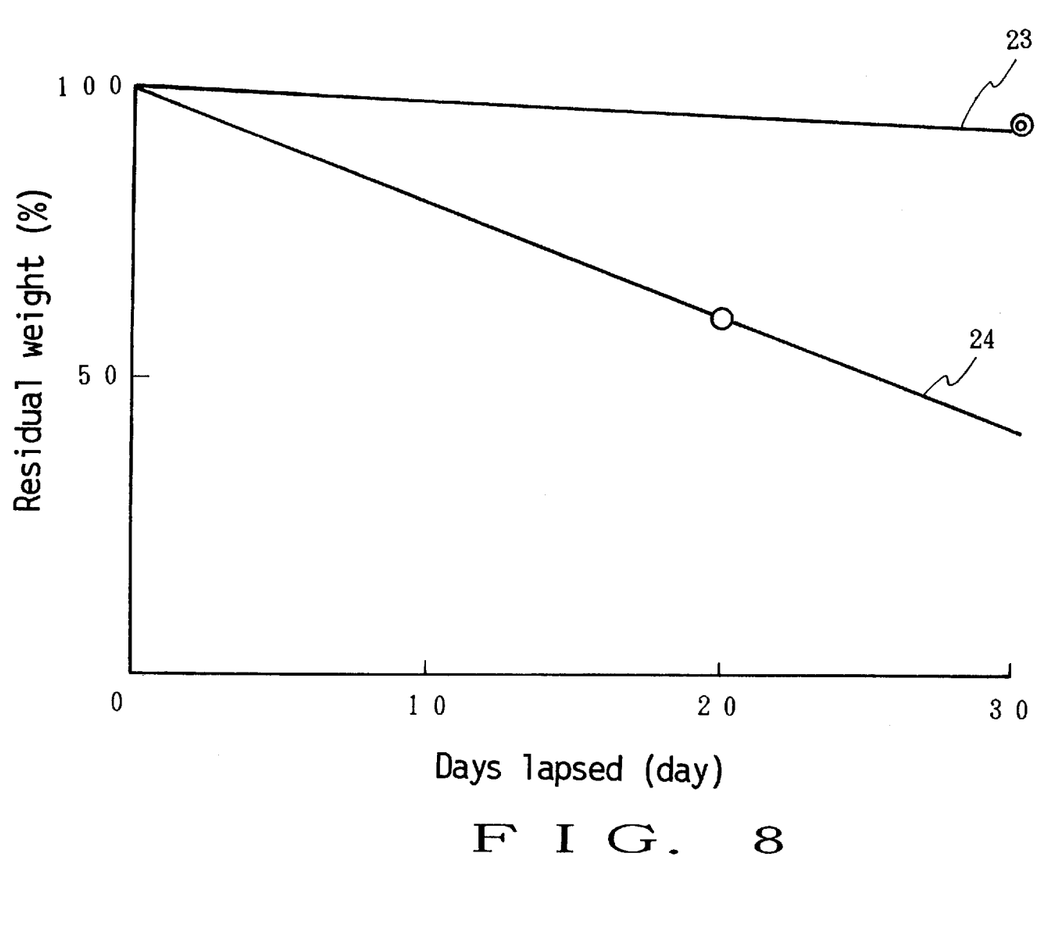
FIG. 8 is a graph showing the release speed of AIT vapor from antimicrobial agents comprising cellulose beads impregnated with AIT (2 g), enclosed in packaging materials having various air permeabilities [21,000 seconds (24 in the Figure) and 400,000 seconds (23 in the Figure)] and an effective surface area of 200 cm².
Figure 9:
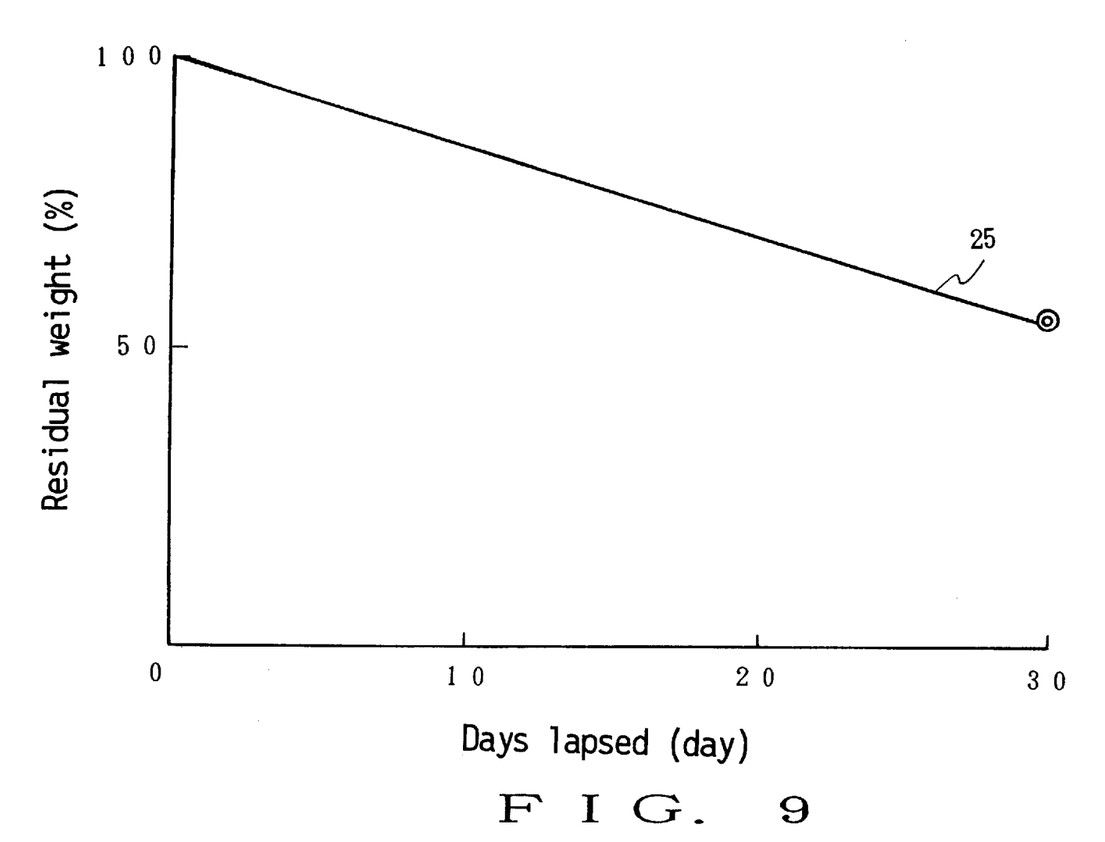
FIG. 9 is a graph showing the release speed of AIT vapor from an antimicrobial agent comprising cellulose beads impregnated with AIT (0.2 g), in a packaging material having an air permeability of 400,000 seconds (25 in the Figure) and an effective surface area of 300 cm².
Figure 10:
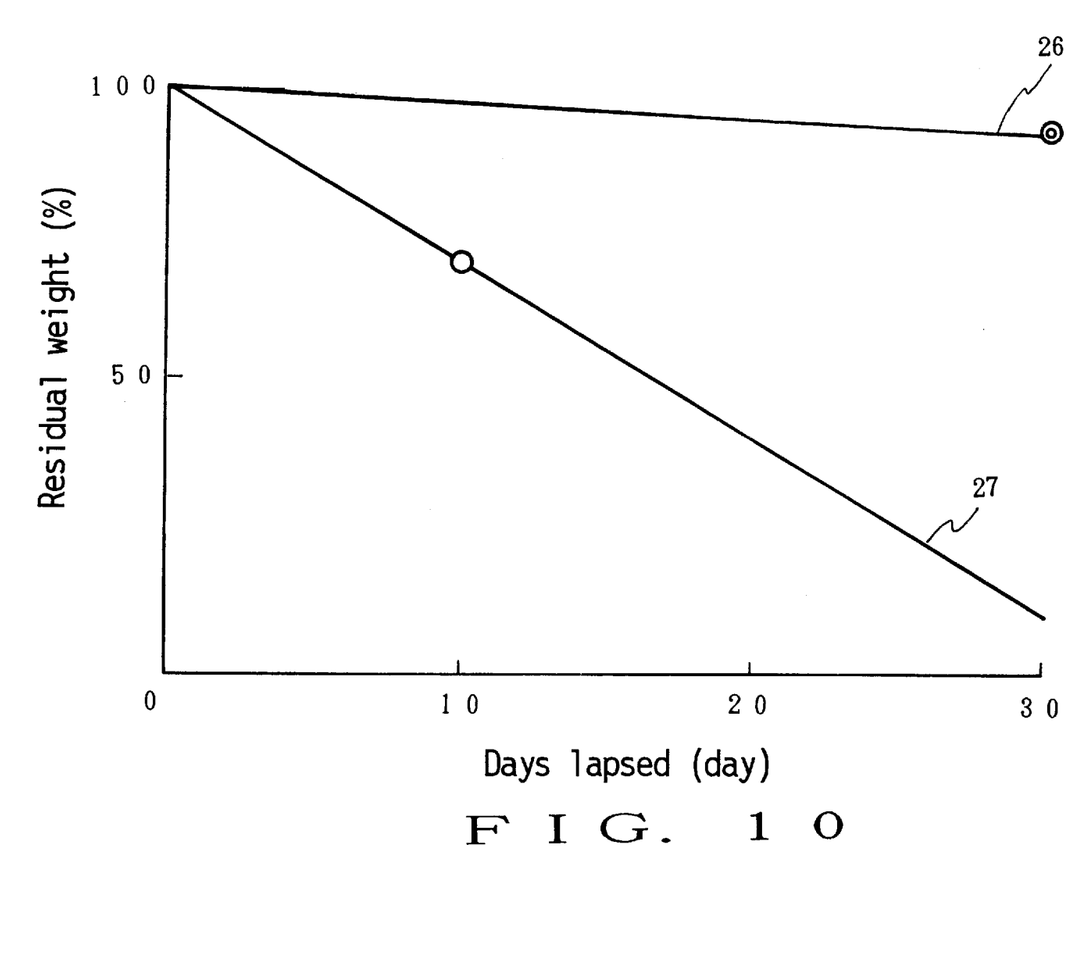
FIG. 10 is a graph showing the release speed of AIT vapor from antimicrobial agents comprising cellulose beads impregnated with AIT (2 g), in packaging materials having various air permeabilities [21,000 seconds (27 in the Figure) and 400,000 seconds (26 in the Figure)] and an effective surface area of 300 cm².

The respective AIT-impregnated supports prepared in Example (4) were placed in Schales in an amount that makes the total AIT 2 g, and left standing in a thermostatic chamber at 30° C. The changes in weight were determined with the lapse of time, based on which the release of the AIT vapor was observed. The results are shown in FIG. 4.

As a result, every support rapidly released AIT vapor and sustained release was not observed.

Experimental Example 4
Control of sustained release and release speed of AIT vapor by cellulose-modified nonwoven fabric The respective antimicrobial agents comprising, as a packaging material, the cellulose-modified nonwoven fabric ④, ⑤ or ⑥ prepared according to Example (2) and shown in the following Table, and AIT-impregnated foamed cellulose beads (0.2 g or 2 g AIT content) therein were placed in a thermo- and humidity-static chamber at 20° C. under 65% RH in such a manner that the agents are not exposed to the wind. The decrease in weight was measured with the lapse of time, from which the residual AIT (%) was obtained.

| packaging material | | viscose concentration (%) | amount of adhered regenerated cellulose (g/m$^2$) | permeation (second) |
|---|---|---|---|---|
| cellulose-modified nonwoven fabric | ④ | 3.2 | 0.7 | 1,500 |
| cellulose-modified nonwoven fabric | ⑤ | 6.2 | 2.1 | 21,000 |
| cellulose-modified nonwoven fabric | ⑥ | 6.8 | 2.8 | 400,000 |

Effective area of packaging material
  (i) 32 cm² (4 cm×4 cm bag, front and back areas 32 cm²)
  (ii) 200 cm² (10 cm×10 cm bag)
  (iii) 300 cm² (10 cm×15 cm bag)
The results are shown in FIGS. 5–10.

Experimental Examples 5–9

Viscose solutions having a different cellulose concentration were roll-coated according to the method of Example (2) on the surface of the packaging substrate 1 (paper) prepared according to Example (1) to give five kinds of packaging materials having different air permeation (500 seconds, 1,000 seconds, 20,000 seconds, 500,000 seconds or 1,000,000 seconds).

Supports impregnated with various amounts of AIT were placed in the packaging materials to give dispensed agents having various effective surface areas, which were subjected to the following experiment.

Experimental Example 5
Antimicrobial effect of antimicrobial agent—①

Foamed cellulose beads impregnated with 600 mg of AIT were placed in packaging materials having the air permeation as shown in the following Table, to give 6×8 cm dispensed agents having an effective surface area of about 38 cm². The agents were placed in an about 100 l thermostatic chamber and left standing at 10° C. At the same time, 10 Schales containing a TCBS medium smeared with a suspension of *Vibrio parahaemolyticus* were placed therein, and the growth of the bacteria was observed by opening the door once a day for 1 month.

| permeation (second) | week 1 | week 2 | week 3 | week 4 |
|---|---|---|---|---|
| 500 | – | – | ± | ± |
| 20000 | – | – | – | – |
| 1000000 | – | ± | + | + |

– : no colony observed
± : colony-like substance little observed
+ : colony observed Experimental Example 6
Antimicrobial effect of antimicrobial agent—②

Cellulose beads impregnated with 0.1 g of AIT were enclosed in packaging materials having an air permeation of 1,000 seconds or 1,000,000 seconds to give antimicrobial agents (effective surface area 1 cm²). As a control, cellulose beads impregnated with AIT were enclosed in a packaging material without viscose processing (permeation about 1 second).

Every preparation was placed in an insulated box containing 5 kg of raw sea urchin eggs (wrapped on a tray) and kept in cold storage.

| permeation | day 1 | day 3 | day 5 |
|---|---|---|---|
| 1000 seconds | – | – | – |
| 1000000 seconds | – | – | – |
| 0 sec | – sea urchin egg near the agent tasted wasabi | – sea urchin egg near the agent tasted wasabi | – sea urchin egg near the agent tasted wasabi |

| permeation | day 7 | day 10 |
|---|---|---|
| 1000 seconds | – | – |
| 1000000 seconds | – | + white yeast |
| 0 sec | – sea urchin egg near the agent tasted wasabi | – the taste of wasabi became a little mild |

Experimental Example 7
Antimicrobial effect of antimicrobial agent—③

Using packaging materials having an air permeation of 500 seconds, 20,000 seconds or 1,000,000 seconds, antimicrobial agents (3×3 cm, effective surface area 21 cm²) containing AIT (100 mg) were prepared. The agents were placed in a box containing 10 kg lemon and left standing at room temperature.

| permeation (seconds) | day 3 | week 1 | week 2 | week 3 |
|---|---|---|---|---|
| 500 | physiological disorder near the agent | physiological disorder near the agent | | |
| 20000 | – | – | – | slight physiological disorder near the agent |
| 1000000 | – | – | mold developed | mold developed |

Experimental Example 8
Antimicrobial effect of antimicrobial agent—④

Using packaging materials coated with regenerated cellulose so that the permeation became 500 seconds, 20,000 seconds or 500,000 seconds, cellulose particles containing 200 mg of AIT were enclosed, thereby to give dispensed agents (4 cm×4 cm, effective surface area 21 cm²).

The agents were placed in a paper shoe box together with a leather shoe previously sprayed with a mold suspension, and stored in a room (25°–30° C.). The development of mold was observed.

| permeation (second) | 1 day later | 4 days later | week 1 | week 2 | week 3 | week 4 |
|---|---|---|---|---|---|---|
| 500 | – | – | ± | + | ++ | ++ |
| | smell of wasabi | smell of wasabi | | | | |
| 20000 | – | – | – | – | – | – |
| 500000 | – | ± | + | ++ | ++ | ++ |

– : mold not observed
± : mold slightly observed
+ : clear development of mold on part of shoe
++ : mold spreading in the entirety of shoe Experimental Example 9
Antimicrobial effect of antimicrobial agent—⑤

AIT-impregnated cellulose beads were placed in a viscose-modified paper having an air permeation of 50,000 seconds, such that AIT was contained in an amount of 10 g, 50 g or 100 g, thereby to prepare dispensed agents having an effective surface area of 300 cm².

The agents were placed in a cardboard box (about 1 m³) together with a leather article (clothing) and stored in a warehouse for 6 months. As a control, a specimen without the agent was prepared and examined for the development of mold. In the Table, the symbols mean the same as in Experimental Example 8.

| content (g) | 1 month | 2 months | 3 months | 4 months | 5 months | 6 months |
|---|---|---|---|---|---|---|
| 10 | – | – | + | + | + | + |
| 50 | – | – | – | – | – | – |
| 100 | – | – | – | – | – | – |
| 0 | ± | + | + | + | + | + |

A mold-suppressive effect was retained when the content was 50 g or 100 g. When 100 g of AIT was used, the smell of AIT remained strong even when the agent was discarded, which means that the AIT was wasted.

What is claimed is:

1. An antimicrobial agent comprising allyl isothiocyanate packaged and enclosed ia a hydrophilic packaging material comprising a porous structure wherein part of the pores of the porous packaging structure is filled with, or said pores are partially or entirely narrowed by a resin impervious to allyl isothiocyanate vapor wherein an air permeation of the packaging material is 1,000 to 500,000 seconds.

2. The antimicrobial agent of claim 1, wherein the resin is a regenerated cellulose.

3. The antimicrobial agent of claim 1, wherein the allyl isothiocyanate is carried by a support.

4. The antimicrobial agent of claim 3, wherein the support is cellulose particles.

5. The antimicrobial agent of claim 4, wherein the allyl isothiocyanate is dissolved in an oily liquid having a vapor pressure of not more than 2 mmHg at 30° C. and is carried by the cellulose particles.

6. The antimicrobial agent of claim 5, wherein the oily liquid comprises a middle chain fatty acid triglyceride.

7. A low temperature storage container containing the antimicrobial agent of any one of claims 1, 2, 3, 4, 5 or 6.

8. A method for providing an antimicrobial effect on a leather article which comprises inserting into or maintaining in close proximity to the leather article the antimicrobial agent of claim 1.

9. A method for providing an antimicrobial effect in a low temperature storage container which comprises inserting therein the antimicrobial agent of claim 1.

10. A container for a leather article, said container containing both a leather article and the microbial agent of any one of claims 1, 2, 3, 4, 5 or 6.

11. A manufactured leather article into which after manufacture the antimicrobial agent of any one of claims 1, 2, 3, 4, 5 or 6 has been inserted.

12. The container for a leather article of claim 10 wherein the leather article is a shoe.

13. The manufactured leather article of claim 11 being a shoe.

14. The antimicrobial agent of claim 1, wherein a perforated film or a polyolefin heat sealing film is laminated on the hydrophilic packaging material.

15. A method for controlling an allyl isothiocyanate vapor release speed, comprising enclosing an allyl isothiocyanate in a hydrophilic packaging material comprising a porous structure wherein part of the pores of a porous packaging substrate is filled with, or said pores are partially or entirely narrowed by a resin impervious to allyl isothiocyanate vapor wherein an air permeation of the packaging material is 1,000 to 500,000 seconds.

16. The method for controlling an allyl isothiocyanate vapor release speed according to claim 15, wherein the resin is a regenerated cellulose.

17. The method for controlling an allyl isothiocyanate vapor release speed according to claim 15, wherein the allyl isothiocyanate is carried by a support.

18. The method for controlling an allyl isothiocyanate vapor release speed according to claim 17, wherein the support is cellulose particles.

19. The method for controlling an allyl isothiocyanate vapor release speed according to claim 18, wherein the allyl isothiocyanate is dissolved in an oily liquid having a vapor pressure of not more than 2 mmHg at 30° C. and is carried by cellulose particles.

20. The method for controlling an allyl isothiocyanate vapor release speed according to claim 19, wherein the oily liquid comprises a middle chain fatty acid triglyceride.

* * * * *